(12) United States Patent
Bioley et al.

(10) Patent No.: US 9,770,411 B2
(45) Date of Patent: Sep. 26, 2017

(54) METHODS OF USING GAS-FILLED MICROVESICLES COVALENTLY BOUND TO AN ANTIGEN

(75) Inventors: Gilles Bioley, Fiez (CH); Blaise Corthesy, Thierrens (CH); Philippe Bussat, Pers-Jussy (FR); Anne Lassus, Carouge (CH); Michel Schneider, Troinex (CH)

(73) Assignee: Bracco Suisse S.A., Manno (CH)

( * ) Notice: Subject to any disclaimer, the term of this patent is extended or adjusted under 35 U.S.C. 154(b) by 504 days.

(21) Appl. No.: 13/996,034

(22) PCT Filed: Dec. 21, 2011

(86) PCT No.: PCT/EP2011/073572
§ 371 (c)(1),
(2), (4) Date: Jun. 20, 2013

(87) PCT Pub. No.: WO2012/085072
PCT Pub. Date: Jun. 28, 2012

(65) Prior Publication Data
US 2013/0295147 A1  Nov. 7, 2013

(30) Foreign Application Priority Data
Dec. 24, 2010 (EP) .................................. 10016078

(51) Int. Cl.
| A61K 39/395 | (2006.01) |
| A61K 9/00 | (2006.01) |
| A61K 39/385 | (2006.01) |
| A61K 47/48 | (2006.01) |
| A61K 39/00 | (2006.01) |

(52) U.S. Cl.
CPC .......... *A61K 9/0087* (2013.01); *A61K 39/385* (2013.01); *A61K 47/48869* (2013.01); *A61K 2039/60* (2013.01)

(58) Field of Classification Search
None
See application file for complete search history.

(56) References Cited

U.S. PATENT DOCUMENTS

| 4,276,885 A | 7/1981 | Tickner et al. |
| 5,271,928 A | 12/1993 | Schneider et al. |
| 5,413,774 A | 5/1995 | Schneider et al. |
| 5,445,813 A | 8/1995 | Schneider et al. |
| 5,556,610 A | 9/1996 | Yan et al. |
| 5,597,549 A | 1/1997 | Schneider et al. |
| 5,605,673 A | 2/1997 | Schutt et al. |
| 5,711,933 A | 1/1998 | Bichon et al. |
| 5,827,504 A | 10/1998 | Yan et al. |
| 6,333,021 B1 | 12/2001 | Schneider et al. |
| 2003/0166521 A1 | 9/2003 | Eppihimer et al. |

FOREIGN PATENT DOCUMENTS

| CN | 100546649 C | 10/2009 |
| EP | 0324938 B1 | 11/1993 |
| EP | 0554213 B1 | 1/1997 |
| EP | 1714642 A1 | 10/2006 |
| WO | 91/15244 A2 | 10/1991 |
| WO | 94/09829 A1 | 5/1994 |
| WO | 97/29782 A1 | 8/1997 |
| WO | 2004/069284 A2 | 8/2004 |
| WO | 2008/131217 A1 | 10/2008 |

OTHER PUBLICATIONS

Database WPI Week 200760 Thomson Scientific, London, GB, AN 2007-625099; XP002634738; Mar. 28, 2007.
Liu, Wen-jun et al., "Identifiction of N-terminal Residues on P-selectin Glycoprotein Ligand-1 Required for Binding to P-selectin", The Journal of Biological Chemistry, The American Society for Biochemistry and Molecular Biology, Inc, US, vol. 273, No. 12, Mar. 20, 1998, pp. 7078-7087, XP002116309, ISSN: 0021-9258.
Reed, Steven G. et al., "New horizons in adjuvants for vaccine development", Trends in Immunology, vol. 30, No. 1, 2008, pp. 23-32, Elsevier Ltd.
Rychak, J.J. et al., "Selectin Ligands Promote Ultrasound Contrast Agent Adhesion under Shear Flow", Molecular Pharmaceutics, vol. 3, No. 5, Oct. 2006, pp. 516.524, XP002612674, ISSN: 1543-8384.
PCT International Search Report for PCT/EP2011/073572, dated Feb. 24, 2012.
PCT Written Opinion for PCT/EP2011/073572, dated Feb. 24, 2012.
Suzuki, Ryo et al., "A novel strategy utilizing ultrasound for antigen delivery in dendritic cell-based cancer immunotherapy", Journal of Controlled Release, vol. 133, No. 3, Feb. 10, 2009, pp. 198-205, XP002634737, ISSN: 1873-4995.
Tanaka, Yuriko et al., "Liposomes with Differential Lipid Components Exert Differential Adjuvanticity in Antigen-Liposome Conjugates via Differential Recognition by Macrophages", Bioconjugate Chem., vol. 15, No. 1, 2004, pp. 35-40.
Wilson-Welder, Jennifer H. et al., "Vaccine Adjuvants: Current challenges and Future Approaches", Journal of Pharmaceutical Sciences, vol. 98, No. 4, Apr. 2009, pp. 1278-1316.
Yanagisawa, Kyosuke et al., "Phagocytosis of ultrasound contrast agent microbubbles by Kupffer cells", Ultrasound in medicine and Biology, New York, NY, US, vol. 33, No. 2, Feb. 14, 2007, pp. 318-325, XP005911769, ISSN: 0301-5629.
PCT International Preliminary Report on Patentability for PCT/EP2011/073572, dated Jul. 4, 2013.

(Continued)

*Primary Examiner* — Yunsoo Kim
(74) *Attorney, Agent, or Firm* — Vivicar Law, PLLC

(57) ABSTRACT

Gas-filled microvesicles comprising an antigen bound thereto and to aqueous suspensions containing said microvesicles, for use in immunomodulating formulations, in particular as a vaccine. The antigen is covalently bound to a component of the microvesicles envelope. The microvesicles of the invention are particularly effective in the uptake by antigen-presenting cells, in particular dendritic cells.

20 Claims, No Drawings

METHODS OF USING GAS-FILLED MICROVESICLES COVALENTLY BOUND TO AN ANTIGEN

CROSS-REFERENCE TO RELATED APPLICATIONS

This application is the national stage application of corresponding international application number PCT/EP2011/073572, filed Dec. 21, 2011, which claims priority to and the benefit of European application no. 10016078.7, filed Dec. 24, 2010, all of which are hereby incorporated by reference in their entirety.

TECHNICAL FIELD

The invention relates in general terms to gas-filled microvesicles comprising an antigen bound thereto and to aqueous suspensions containing said microvesicles, for use in particular in vaccine and in immunomodulating formulations.

BACKGROUND OF THE INVENTION

Dendritic cells (DC) play a pivotal role in the initiation and modulation of adaptive immunity through the release of polarizing cytokines, as well as the processing and presentation of captured antigen (Ag) to prime or recall specific T cell responses. Immunotherapy strategies, including vaccination, aiming at modulating immune responses, have been focusing on the delivery of Ag to these professional antigen-presenting cells (APC). Vaccination is usually achieved by the in vivo delivery of antigenic entities (DNA, peptides or proteins), that are, due to their low immunological activities, generally formulated in adjuvanted delivery systems.

Several delivery systems have been investigated during the past years, where different adjuvants, based in particular on Ag particulation, have been tested for their efficacy in possibly enhancing antigen delivery and thus activating the immune system. For instance, the adjuvant effect of liposomes in antigen-liposomes formulations has been investigated (see e.g.: Tanaka et al, "Liposomes with Differential Lipid Components Exert Differential Adjuvanticity in Antigen-Liposome Conjugates via Differential Recognition by Macrophages", *Bioconjugate Chem.*, Vol. 15 (1), 2004, pp. 35-40). More recently, also gas-filled microvesicles have been proposed as immune adjuvants and vaccine carriers, as disclosed in Chinese Patent CN 10054664. Gas-filled microvesicles are generally known for their use as contrast agents, particularly for ultrasound imaging. They typically include suspensions of gas bubbles having a diameter of a few microns dispersed in an aqueous medium and comprise suitable materials forming a stabilizing envelope for containing the gas.

CN 10054664 discloses in particular the preparation of gas-filled microvesicles where an antigen is either encapsulated inside the microvesicle or adhered to the surface thereto (by static electrical adsorption). The microvesicles are then administered topically and ultrasonic waves are applied locally, to destroy the microvesicles and release the antigen. According to said patent, contrary to the positive effects observed with combined use of gas-filled microvesicles and ultrasound irradiation, the sole administration of microvesicles with an antigen adhered thereto is substantially ineffective (comparable to a blank control).

The Applicant has now found that by preparing gas-filled microvesicles where the antigen is covalently bound to a component of the microvesicle envelope, in particular a phospholipid, a remarkable adjuvant effect of the microvesicle can be observed in the substantial absence of any ultrasound irradiation (e.g. with no ultrasound irradiation), thus allowing an effective uptake of the antigen by antigen-presenting cells, in particular dendritic cells, in order to enhance/modulate antigen-specific immune responses

SUMMARY OF THE INVENTION

An aspect of the invention relates to a pharmaceutical formulation comprising gas-filled microvesicles with a stabilizing envelope, said microvesicles comprising an antigen covalently bound to a component of said envelope, for use in an immunomodulating treatment.

According to a preferred aspect, said immunomodulating treatment comprises vaccination.

In a preferred embodiment, said formulation is an aqueous suspension comprising said microvesicles.

According to a further preferred embodiment, said antigen is a vaccine antigen.

According to another aspect, the invention relates to the use of an aqueous suspension of gas-filled microvesicles comprising an antigen covalently bound to a component of said microvesicles for preparing a vaccine or an immunomodulating agent.

Another aspect of the invention relates to a method for increasing the uptake of an antigen by a respective antigen-presenting cell, which comprises contacting said antigen with said cell wherein said antigen is covalently bound to a gas-filled microvesicle. According to a preferred embodiment, said antigen-presenting cell is a dendritic cell.

A further aspect of the invention relates to a method for inducing modulation of the immune system in a patient in need thereof which comprises administering to said patient an effective amount of an aqueous suspension of gas-filled microvesicles comprising an antigen covalently bound to a component of said microvesicles.

According to a preferred embodiment, said stabilizing envelope comprises an immunomodulating adjuvant.

DETAILED DESCRIPTION OF THE INVENTION

The term "gas-filled microvesicles" includes any structure comprising bubbles of gas of micronic or nanometric size surrounded by an envelope or layer (including film-form layers) of a stabilizing material. The term includes what is known in the art as gas-filled liposomes, microbubbles, microspheres, microballoons or microcapsules. The stabilizing material can be any material typically known in the art including, for instance, surfactants, lipids, sphingolipids, oligolipids, glycolipids, phospholipids, proteins, polypeptides, carbohydrates, and synthetic or natural polymeric materials.

The term "precursor" of a gas-filled microvesicle includes any composition which, upon reconstitution with an aqueous carrier in the presence of a gas, will produce a suspension of gas-filled microvesicles. Said compositions typically include any of the above-cited stabilizing materials in dry powdered form (e.g. freeze-dried or spray-dried) capable of forming gas-filled microvesicles upon shaking an aqueous suspension thereof in the presence of a gas.

The term "microbubbles" includes aqueous suspensions in which the bubbles of gas are bounded at the gas/liquid interface by a very thin envelope (film) involving a stabilizing amphiphilic material disposed at the gas to liquid interface (sometimes referred to in the art as an "evanescent" envelope). Microbubble suspensions can be prepared by contacting a suitable precursor thereof, such as powdered amphiphilic materials (e.g. freeze-dried preformed liposomes or freeze-dried or spray-dried phospholipid solutions) with air or other gas and then with an aqueous carrier, while agitating to generate a microbubble suspension which can then be administered, preferably shortly after its preparation. Examples of aqueous suspensions of gas microbubbles, of precursors and of the preparation thereof are disclosed, for instance, in U.S. Pat. Nos. 5,271,928, 5,445,813, 5,413,774, 5,556,610, 5,597,549, 5,827,504 and WO 04/069284, which are here incorporated by reference.

The terms "microballoons" or "microcapsules" include suspensions in which the bubbles of gas are surrounded by a solid material envelope of a lipid or of natural or synthetic polymers. Examples of microballoons and of the preparation thereof are disclosed, for instance, in U.S. Pat. Nos. 5,711,933 and 6,333,021, here incorporated by reference.

The phrase "envelope-forming moiety" includes any moiety which is capable of participating to the formation of the stabilizing envelope of gas-filled microvesicles. Said moiety is preferably an amphiphilic material, preferably comprising a phospholipid.

The term "immunomodulation" or "modulation of immune response" comprises within its meanings any medical treatment ("immunomodulating treatment") directed to or capable of inducing immunostimulation and/or tolerance in a patient in need thereof. Similarly, the term "immunomodulator" or "immunomodulating" compound or formulation is intended to comprise immunostimulating and/or tolerogenic compounds or formulations, capable of inducing the desired modulation of the immune response in the patient.

The term "immunostimulation" comprises any increase in the immunogenicity of the response of a patient. Similarly "immunostimulating" compounds or formulations comprise compounds or formulations capable of increasing said immune response (useful, for instance, in the treatment of infections, cancers and/or immunodeficiency diseases).

The term "tolerance" comprises within its meanings any state of substantial non-responsiveness of the immune system of a patient to an antigen. "Tolerogens" includes compounds or formulations capable of inducing tolerance to an antigen in a patient (useful for instance, in the treatment of allergies, such as environmental—e.g. pollen—allergies or nutritional allergies).

The term "vaccination" comprises any immunomodulating treatment comprising the administration of an antigen compound or formulation, typically a vaccine antigen, to a patient. Similarly, the term vaccine comprises within its meanings any compound or formulation comprising a vaccine antigen The term "(medical) treatment" comprises within its meaning either prophylactic treatment and/or therapeutic treatment.

Gas-filled microvesicles according to the invention can be any microvesicle known in the art, including gas-filled microbubbles, microcapsules and microballoons.

Gas-filled microbubbles are generally stabilized by one or more amphiphilic component. Amphiphilic components suitable for forming a stabilizing envelope of microbubbles comprise, for instance, phospholipids; lysophospholipids; fatty acids, such as palmitic acid, stearic acid, arachidonic acid or oleic acid; lipids bearing polymers, such as chitin, hyaluronic acid, polyvinylpyrrolidone or polyethylene glycol (PEG), also referred as "pegylated lipids"; lipids bearing sulfonated mono- di-, oligo- or polysaccharides; cholesterol, cholesterol sulfate or cholesterol hemisuccinate; tocopherol hemisuccinate; lipids with ether or ester-linked fatty acids; polymerized lipids; diacetyl phosphate; dicetyl phosphate; ceramides; polyoxyethylene fatty acid esters (such as polyoxyethylene fatty acid stearates), polyoxyethylene fatty alcohols, polyoxyethylene fatty alcohol ethers, polyoxyethylated sorbitan fatty acid esters, glycerol polyethylene glycol ricinoleate, ethoxylated soybean sterols, ethoxylated castor oil or ethylene oxide (EO) and propylene oxide (PO) block copolymers; sterol aliphatic acid esters including, cholesterol butyrate, cholesterol iso-butyrate, cholesterol palmitate, cholesterol stearate, lanosterol acetate, ergosterol palmitate, or phytosterol n-butyrate; sterol esters of sugar acids including cholesterol glucuronides, lanosterol glucuronides, 7-dehydrocholesterol glucuronide, ergosterol glucuronide, cholesterol gluconate, lanosterol gluconate, or ergosterol gluconate; esters of sugar acids and alcohols including lauryl glucuronide, stearoyl glucuronide, myristoyl glucuronide, lauryl gluconate, myristoyl gluconate, or stearoyl gluconate; esters of sugars with aliphatic acids including sucrose laurate, fructose laurate, sucrose palmitate, sucrose stearate, glucuronic acid, gluconic acid or polyuronic acid; saponins including sarsasapogenin, smilagenin, hederagenin, oleanolic acid, or digitoxigenin; glycerol or glycerol esters including glycerol tripalmitate, glycerol distearate, glycerol tristearate, glycerol dimyristate, glycerol trimyristate, glycerol dilaurate, glycerol trilaurate, glycerol dipalmitate,; long chain alcohols including n-decyl alcohol, lauryl alcohol, myristyl alcohol, cetyl alcohol, or n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-β-D-mannopyranoside; 12-(((7'-diethylaminocoumarin-3-yl)carbonyl)methylamino) octadecanoic acid; N-[12-(((7'-diethylaminocoumarin-3-yl)carbonyl)methylamino)octadecanoyl]-2-aminopalmitic acid; N-succinyldioleylphosphatidylethanolamine; 1,2-dioleyl-sn-glycerol; 1,2-dipalmitoyl-sn-3-succinylglycerol; 1,3-dipalmitoyl-2-succinylglycerol; 1-hexadecyl-2-palmitoyl-glycerophosphoethanolamine or palmitoylhomocysteine; alkylamines or alkylammonium salts, comprising at least one ($C_{10}$-$C_{20}$), preferably ($C_{14}$-$C_{18}$), alkyl chain, such as, for instance, N-stearylamine, N,N'-distearylamine, N-hexadecylamine, N,N'-dihexadecylamine, N-stearylammonium chloride, N,N'-distearylammonium chloride, N-hexadecylammonium chloride, N,N'-dihexadecylammonium chloride, dimethyldioctadecylammonium bromide (DDAB), hexadecyltrimethylammonium bromide (CTAB); tertiary or quaternary ammonium salts comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP); and mixtures or combinations thereof.

According to a preferred embodiment, at least one of the compounds forming the microbubbles' envelope is a phospholipid, optionally in admixture with any of the other above cited materials. According to the present description, the term phospholipid is intended to encompass any amphiphilic phospholipid compound, the molecules of which are capable of forming a stabilizing film of material (typically in the form of a mono-molecular layer) at the gas-water boundary interface in the final microbubbles suspension. Accordingly, these materials are also referred to in the art as "film-forming phospholipids".

Amphiphilic phospholipid compounds typically contain at least one phosphate group and at least one, preferably two, lipophilic long-chain hydrocarbon group. Examples of suitable phospholipids include esters of glycerol with one or preferably two (equal or different) residues of fatty acids and with phosphoric acid, wherein the phosphoric acid residue is in turn bound to a hydrophilic group, such a, for instance, choline (phosphatidylcholines-PC), serine (phosphatidylserines-PS), glycerol (phosphatidylglycerols-PG), ethanolamine (phosphatidylethanolamines-PE), inositol (phosphatidylinositol). Esters of phospholipids with only one residue of fatty acid are generally referred to in the art as the "lyso" forms of the phospholipid or "lysophospholipids". Fatty acids residues present in the phospholipids are in general long chain aliphatic acids, typically containing from 12 to 24 carbon atoms, preferably from 14 to 22; the aliphatic chain may contain one or more unsaturations or is preferably completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. Preferably, saturated fatty acids such as myristic acid, palmitic acid, stearic acid and arachidic acid are employed.

Further examples of phospholipid are phosphatidic acids, i.e. the diesters of glycerol-phosphoric acid with fatty acids; sphingolipids such as sphingomyelins, i.e. those phosphatidylcholine analogs where the residue of glycerol diester with fatty acids is replaced by a ceramide chain; cardiolipins, i.e. the esters of 1,3-diphosphatidylglycerol with a fatty acid; glycolipids such as gangliosides GM1 (or GM2) or cerebrosides; glucolipids; sulfatides and glycosphingolipids.

As used herein, the term phospholipids include either naturally occurring, semisynthetic or synthetically prepared products that can be employed either singularly or as mixtures.

Examples of naturally occurring phospholipids are natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins. Preferred phospholipids are fatty acids di-esters of phosphatidylcholine, ethylphosphatidylcholine, phosphatidylglycerol, phosphatidic acid, phosphatidylethanolamine, phosphatidylserine, phosphatidylinositol or of sphingomyelin.

Examples of preferred phospholipids are, for instance, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleylphosphatidylcholine (POPC), 1-oleyl-2-palmitoyl-phosphatidylcholine (OPPC), dilauroyl-phosphatidylglycerol (DLPG) and its alkali metal salts, diarachidoylphosphatidyl-glycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidyl-glycerol (DSPG) and its alkali metal salts, dioleoyl-phosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoyl-phosphatidic acid (DAPA) and its alkali metal salts, dimyristoyl-phosphatidylethanolamine (DMPE), dipalmitoylphosphatidylethanolamine (DPPE), distearoyl phosphatidylethanolamine (DSPE), dioleylphosphatidyl-ethanolamine (DOPE), diarachidoylphosphatidyl-ethanolamine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), dioleoyl-phosphatidylinositol (DOPI).

Suitable phospholipids further include phospholipids modified by linking a hydrophilic polymer, such as polyethyleneglycol (PEG) or polypropyleneglycol (PPG), thereto. Preferred polymer-modified phospholipids include "pegylated phospholipids", i.e. phospholipids bound to a PEG polymer. Examples of pegylated phospholipids are pegylated phosphatidylethanolamines ("PE-PEGs" in brief) i.e. phosphatidylethanolamines where the hydrophilic ethanolamine moiety is linked to a PEG molecule of variable molecular weight (e.g. from 300 to 20000 daltons, preferably from 500 to 5000 daltons), such as DPPE-PEG (or DSPE-PEG, DMPE-PEG, DAPE-PEG or DOPE-PEG). For example, DPPE-PEG2000 refers to DPPE having attached thereto a PEG polymer having a mean average molecular weight of about 2000.

Particularly preferred phospholipids are DAPC, DSPC, DPPC, DMPA, DPPA, DSPA, DMPG, DPPG, DSPG, DMPS, DPPS, DSPS and Ethyl-DSPC. Most preferred are DPPG, DPPS and DSPC.

Mixtures of phospholipids can also be used, such as, for instance, mixtures of DPPE and/or DSPE (including pegylated derivates), DPPC, DSPC and/or DAPC with DSPS, DPPS, DSPA, DPPA, DSPG, DPPG, Ethyl-DSPC and/or Ethyl-DPPC.

According to an embodiment of the invention, the phospholipid is the main component of the stabilizing envelope of microbubbles, amounting to at least 50% (w/w) of the total amount of components forming the envelope of the gas filled microbubbles, preferably at least 75%. In some of the preferred embodiments, substantially the totality of the envelope (i.e. at least 90% w/w) can be formed of phospholipids.

The phospholipids can conveniently be used in admixture with any of the above listed amphiphilic compounds. Thus, for instance, lipids such as cholesterol, ergosterol, phytosterol, sitosterol, lanosterol, tocopherol, propyl gallate or ascorbyl palmitate, fatty acids such as myristic acid, palmitic acid, stearic acid, arachidic acid and derivatives thereof or butylated hydroxytoluene and/or other non-phospholipid compounds can optionally be added to one or more of the foregoing phospholipids, e.g in proportions preferably ranging from zero to 50% by weight, more preferably up to 25%. Particularly preferred is palmitic acid.

The antigen is covalently bound to the stabilizing envelope of the microbubble according to conventional methods, in particular by covalently binding the antigen to an amphiphilic component forming the stabilizing envelope of the microbubble (in brief "envelope-forming component"). Said component can be selected among those previously illustrated, particularly preferred being phospholipids, in particular phosphatidylethanolamines (e.g. DSPE or DPPE). The antigen can be linked directly to the envelope-forming component, e.g. by means of a covalent bond involving reactive groups contained in the respective components, thus obtaining a construct comprising the antigen linked to the envelope-forming. Alternatively, a spacer component can be introduced between the antigen and the envelope-forming component, to obtain an antigen/spacer/envelope-forming-component construct. Examples of suitable spacers include, for instance, hydrophilic synthetic polymers such as, polyethyleneglycol, polyvinylpyrrolidone, polyacrylic acid, polyhydroxymethyl acrylate. Preferably, polyethyleneglycol (PEG) is employed. The synthetic polymer may include from 2 to about 500 monomer units, preferably from about 12 to about 250 and even more preferably from about 20 to about 130 monomer units.

The reacting components may either contain the desired reactive groups or can be modified ("functionalized") according to conventional techniques to include the desired reactive group into the component.

For instance, if one of the two reacting components includes a reactive amino group, it can be reacted with the other component containing a suitable corresponding reactive moiety, such as an isothiocyanate group (to form a thiourea bond), a reactive ester (to form an amide bond), or an aldehyde group (to form an imine bond, which may be reduced to an alkylamine bond). Alternatively, if one of the two reacting components includes a reactive thiol group, suitable complementary reactive moieties on the other component may include haloacetyl derivatives, maleimides (to form a thioether bond) or a mixed disulfide comprising a sulphide in the form of a 2-pyridylthio group which upon reaction with a thiol derived from the thiol-bearing component results in the formation of a stable disulfide bond between the two components. Furthermore, if one of the two reacting components includes a reactive carboxylic group, suitable reactive moieties on the other component can be amines and hydrazides (to form amide or N-acyl, N'-alkylhydrazide functions). For example, one may prepare a maleimide-derivatized phospholipid (e.g. phosphatidylethanolamine) which is then reacted with a mercaptoacetylated antigen (e.g. a protein), previously incubated in a deacetylation solution. As another example, one may prepare a maleimide-derivatized pegylated phospholipid (e.g. DSPE-PEG2000-maleimide) which is then reacted with a antigen (e.g. a protein), which has an accessible thiol function, e.g. obtained by first reacting the protein with ((Sulfosuccinimidyl 6-[3'-(2-pyridyldithio)propionamido]-hexanoate) (Sulfo-LC-SDPD) and reducing the disulphide bond by adding tris(2-carboxy-ethyl)phosphine (TCEP).

Antigens, in particular vaccine antigens, which can be covalently bound to a gas-filled microvesicle in a system according to the invention include, but are not limited to natural, recombinant or synthetic products, as well as fragments thereof. Suitable antigens, in particular vaccine antigens, may include, for instance: allergenic antigens derived from or associated with, for instance, plant pollen, insect venom (e.g. Phospholipase A2 from *Apis mellifera*), food, animal dander, dust mites; viral antigens derived from or associated with, for instance, adenovirus, alphavirus, corona virus, cytomegalovirus, distemper, enterovirus species, Epstein Barr virus, flavivirus, hepatitis A, hepatitis B, hepatitis E, herpes species, HIV-1, HIV-2, HTLV 1, human retrovirus species, influenza, lymphocytic choriomeningitis virus, measles, papilloma virus, parainfluenza virus, paramyxovirus, parovirus, poliomyelitis, polyoma tumor virus, rabies, reovirus, togavirus, varicella-zoster virus; bacterial antigens derived from or associated with, for instance, *Bordetella pertussis, Borrelia burgdirferi, brucella* species, chlamydia, *anaplasmataceae enterobacter* species, *Escherichia coli, haemophilus* species, *Helicobacter pylon Klebsiella pneumonia,* legionellosis, menigococcus, *mycobacteria* species, *Neisseria gonorrhoeae, pasturella* species, pneumococci, pseudomonas, ricksettia, *salmonella* species, staphylococci, streptococci, *Treponema palladium,* vivrio, *Yersinia enterocolitica;* fungal antigen derived from or associated with, for instance, *Coccidioides immiti,* histoplasmin, trichophytin, dermatophytin, *Aspergillus fumigatus, Candida albicans, Cladosporium herbarum, Pneumocystis jirovecii;* toxin-derived antigen, derived from or associated with, for instance, *Bordetella pertussis, Clostridium botulinum, Clostridium tetani, Clostridium tetani;* parasitic antigens, derived from or associated with, for instance, coccidian, filarial nematodes, leishmania, plasmodium, sarcocystis, schistosoma, taenia, *Toxoplasma gondii, Trichinella spiralis, Trichomonas vaginalis,* trypanosomes; self antigens, such as those responsible, for instance, for diabetes mellitus type 1, coeliac disease, systemic lupus erythematosis, rheumatoid arthritis, Grave's Disease, Idiopathic thrombocytopenic purpura, Sjögren's syndrome, chronic lymphocytic thyroiditis; or tumor antigens such as, for instance, tyrosinase, Melan-A/MART-1 or other melanoma-associated antigen, cancer/testis antigens, carcinogenic embryonic antigen, polymorphic epithelial mucins, epithelial cellular adhesion molecule, human papilloma virus, prostate-specific agent or alpha-fetoprotein.

The amount of antigen bound to the microvesicle's envelope can vary depending from the type of antigen and from the type of immunomodulation which has to be induced in the patient. For instance, the antigen may vary from about 0.1% to about 20% by moles, with respect to the total amount of components forming the microvesicle's envelope. Preferably, said amount can vary from about 0.2% to about 10% by moles and even more preferably from about 0.5% to about 5% by moles.

In a preferred embodiment, the gas-filled microvesicles may advantageously comprise an immunomodulating compound (adjuvant), preferably amphiphilic, for increasing/modifying the adjuvant effect of the microvesicles. As a matter of fact, the addition in the formulation of suitable immunomodulating adjuvants may not only boost the immune response but can also modify its characteristics. Thus, some adjuvants will preferably activate type 2 T lymphocytes (Th2) while others will preferably activate type 1 T lymphocytes (Th1). Some adjuvants may also favor some aspects of the immune response such as for instance the delayed-type hypersensitivity or the response to cytotoxic T lymphocytes, while some others may influence the isotype of immunoglobulins produced. Examples of adjuvants are disclosed, for instance, by Reed S G , Bertholet S, Coler R N et al., "New horizons in adjuvants for vaccine development. Trends in immunology 2008", 30(1): 23-32; or by Wilson-Welder J H, Torres M, Kipper M J et al., "Vaccine Adjuvants: Current challenges and Future Approaches", J Pharm Sci 2009; 98(4):1278-1316. Preferred examples of immunomodulating compounds are TLR (Toll-Like Receptors) ligands, including bacterial lipopeptides, lipoprotein and lipoteichoic acid (LTA), mycobacterial lipoglycan, yeast zymosan, porin, muramyl-di and tri-peptides and derivatives (MTP-PE, threonyl MDP, GMDP, DTP-GDP), di-or tri acylated lipopeptides, such as Pam3CSK4 or Pam2CSK4 (InvivoGen), macrophage activating lipopeptide-2 (MALP-2), Pam2Cys; viral double stranded RNA; liposaccharides such as Theramide™, murapalmitine, mannide oleate (MONTANIDE ISA 51, MONTANIDE ISA 720), sorbitan trioleate; lipopolysaccharide (LPS), Lipid A, monophosphoryl lipid A (MPLA), AGPs; flagellin; viral single stranded RNA, imidazoquinolines; bacterial DNA, CpG-containing oligodeoxynucleotides (CpG ODN), hemozoin, nucleoside analogs imiquimod and resiquimod; imidazoquinolones such as resiquimod and imiquimod; uropathogenic bacteria, protozoan profiling. Other adjuvant compounds may include toxins (including inactivated and/or labile toxins), e.g. the cholera toxins, including the cholera toxin B subunit (*Vibrio cholerae*), the cholera holotoxin, the cholera toxin A1 subunit, the Tetanus toxin, the inactivated toxin of *Bordetela pertussis* and the labile toxin of *Escherichia coli*; CpG-containing oligodesoxynucleotides (CpG ODN); saponins such as QS-7, QS-21, Quil-A; cytokines such as interferon α, (IFNα), interferon γ, GM-CSF (Granulocyte Macrophage Colony Stimulating Factor), interleukin-2 (IL-2), interleukin 1β, interleukin-7, interleukin-12; lipophilic amines such as DDA (dimethyldioctadecylammonium bromide or chloride), N,N dioctadecyl-N',N'bis(2-hydroxyethyl)propane diamine (Avridine®); imidazoquinolones such as resiquimod and imiquimod; N and synthetic mono- or poly-saccharides such as dextrans, mannans, glucans or gamma inulin; glycolipids such as BAY R1005; polymers such as polyphosphazene (Adjumer™); calcitriol and mixtures thereof Adjuvant vehicles can further be included in the formulation of the invention; these may include mineral salts (eg alum, calcium phosphate), emulsions (for instance squalene- (or squalene-)-in-water emulsion (MF59)), oil-in-water emulsions (AS03, Montanide ISA-51 and ISA-720), liposomes, virosomes, immunostimulatory complexes (ISCOMs), polymeric microspheres, chitosan and the like.

Any of the above adjuvant compounds can be used either alone or in admixture (blend) with any of the other adjuvants. Examples of adjuvant blends include the complete Freund's adjuvant, SAF-21 (which is made of threonyl-MDP and a squalene-in-water emulsion), Walter Reed liposomes which contain lipid A adsorbed to aluminium hydroxide, AS01 which is made of MPLA, liposomes and QS21. Other examples include biodegradable polymeric particles containing MPLA, CpG DNA motifs or other immuno-modulating molecules.

The amount of immunomodulating adjuvant in the stabilizing envelope may vary from about 0.1% to about 50% by mole, preferably from about 0.5% to about 20% and even more preferably from about 1% to about 10% by mole (with respect to the total molar amount of the materials forming the stabilizing envelope).

Other excipients or additives may be present either in the dry formulation of the microbubbles or may be added together with the aqueous carrier used for the reconstitution thereof, without necessarily being involved (or only partially involved) in the formation of the stabilizing envelope of the microbubble. These include pH regulators, osmolality adjusters, viscosity enhancers, emulsifiers, bulking agents, etc. and may be used in conventional amounts. For instance compounds like polyoxypropylene glycol and polyoxyethylene glycol as well as copolymers thereof can be used. Examples of viscosity enhancers or stabilizers are compounds selected from linear and cross-linked poly- and oligo-saccharides, sugars and hydrophilic polymers such as polyethylene glycol.

As the preparation of gas-filled microbubbles may involve a freeze drying or spray drying step, it may be advantageous to include in the formulation a lyophilization additive, such as an agent with cryoprotective and/or lyoprotective effect and/or a bulking agent, for example an amino-acid such as glycine; a carbohydrate, e.g. a sugar such as sucrose, mannitol, maltose, trehalose, glucose, lactose or a cyclodextrin, or a polysaccharide such as dextran, chitosan and its derivatives (for example: carboxymethyl chitosan, trimethyl chitosan); or a polyoxyalkyleneglycol such as polyethylene glycol.

The microbubbles of a composition according to the invention can be produced according to any known method in the art. Typically, the manufacturing method involves the preparation of a dried powdered material comprising an amphiphilic material as indicated above, preferably by lyophilization (freeze drying) of an aqueous or organic suspension comprising said material.

For instance, as described in WO 91/15244, film-forming amphiphilic compounds can be first converted into a lamellar form by any method employed for formation of liposomes. To this end, an aqueous solution comprising the film forming lipids and optionally other additives (e.g. viscosity enhancers, non-film forming surfactants, electrolytes etc.) can be submitted to high-speed mechanical homogenisation or to sonication under acoustic or ultrasonic frequencies, and then freeze dried to form a free flowing powder which is then stored in the presence of a gas. Optional washing steps, as disclosed for instance in U.S. Pat. No. 5,597,549, can be performed before freeze drying.

According to an alternative embodiment (described for instance in U.S. Pat. No. 5,597,549) a film forming compound and a hydrophilic stabiliser (e.g. polyethylene glycol, polyvinyl pyrrolidone, polyvinyl alcohol, glycolic acid, malic acid or maltol) can be dissolved in an organic solvent (e.g. tertiary butanol, 2-methyl-2-butanol or $C_2Cl_4F_2$) and the solution can be freeze-dried to form a dry powder.

Preferably, as disclosed for instance in International patent application WO2004/069284, a phospholipid (selected among those cited above and including at least one of the above-identified charged phospholipids) and a lyoprotecting agent (such as those previously listed, in particular carbohydrates, sugar alcohols, polyglycols, polyoxyalkylene glycols and mixtures thereof) can be dispersed in an emulsion of water with a water immiscible organic solvent (e.g. branched or linear alkanes, alkenes, cyclo-alkanes, aromatic hydrocarbons, alkyl ethers, ketones, halogenated hydrocarbons, perfluorinated hydrocarbons or mixtures thereof) under agitation. The emulsion can be obtained by submitting the aqueous medium and the solvent in the presence of at least one phospholipid to any appropriate emulsion-generating technique known in the art, such as, for instance, sonication, shaking, high pressure homogenization, micromixing, membrane emulsification, high speed stirring or high shear mixing. For instance, a rotor-stator homogenizer can be employed, such as Polytron® PT3000. The agitation speed of the rotor-stator homogenizer can be selected depending from the components of the emulsion, the volume of the emulsion, the relative volume of organic solvent, the diameter of the vessel containing the emulsion and the desired final diameter of the microdroplets of solvent in the emulsion. Alternatively, a micromixing technique can be employed for emulsifying the mixture, e.g. by introducing the organic solvent into the mixer through a first inlet (at a flow rate of e.g. 0.05-5 mL/min), and the aqueous phase a second inlet (e.g. at a flow rate of 2-100 mL/min). Depending on the emulsion technique, the organic solvent can be introduced gradually during the emulsification step or at once before starting the emulsification step. Alternatively the aqueous medium can be gradually added to the water immiscible solvent during the emulsification step or at once before starting the emulsification step. Preferably, the phospholipid is dispersed in the aqueous medium before this latter is admixed with the organic solvent. Alternatively, the phospholipid can be dispersed in the organic solvent or it may be separately added the aqueous-organic mixture before or during the emulsification step. The so obtained microemulsion, which contains microdroplets of solvent surrounded and stabilized by the phospholipid material (and optionally by other amphiphilic film-forming compounds and/or additives), is then lyophilized according to conventional techniques to obtain a lyophilized material, which is stored (e.g. in a vial in the presence of a suitable gas) and which can be reconstituted with an aqueous carrier to finally give a gas-filled microbubbles suspension where the dimensions and size distribution of the microbubbles are substantially comparable with the dimensions and size distribution of the suspension of microdroplets.

A further process for preparing gas-filled microbubbles comprises generating a gas microbubble dispersion by submitting an aqueous medium comprising a phospholipid (and optionally other amphiphilic film-forming compounds and/or additives) to a controlled high agitation energy (e.g. by means of a rotor stator mixer) in the presence of a desired gas and subjecting the obtained dispersion to lyophilisation to yield a dried reconstitutable product. An example of this process is given, for instance, in WO97/29782, here enclosed by reference.

Spray drying techniques (as disclosed for instance in U.S. Pat. No. 5,605,673) can also be used to obtain a dried powder, reconstitutable upon contact with physiological aqueous carrier to obtain gas-filled microbubbles.

The dried or lyophilized product obtained with any of the above techniques will generally be in the form of a powder or a cake, and can be stored (e.g. in a vial) in contact with the desired gas. The product is readily reconstitutable in a suitable physiologically acceptable aqueous liquid carrier, which is typically injectable, to form the gas-filled microbubbles, upon gentle agitation of the suspension. Suitable physiologically acceptable liquid carriers are sterile water, aqueous solutions such as saline (which may advantageously be balanced so that the final product for injection is not hypotonic), or solutions of one or more tonicity adjusting substances such as salts or sugars, sugar alcohols, glycols or other non-ionic polyol materials (eg. glucose, sucrose, sorbitol, mannitol, glycerol, polyethylene glycols, propylene glycols and the like), chitosan derivatives, such as carboxymethyl chitosan, trimethyl chitosan or gelifying compounds, such as carboxymethylcellulose hydroxyethyl starch or dextran.

According to an embodiment of the invention, the construct comprising the antigen (i.e. an antigen/envelope-forming-component construct or an antigen/spacer/envelope-forming-component construct) can be admixed as such with the other components of the formulation, so to be incorporated into the stabilizing envelope upon reconstitution of the freeze-dried material obtained according to any of the above preparation methods.

Alternatively, the construct can be admixed as a suitably functionalized intermediate (e.g. a functionalized envelope-forming component such as a maleimide-containing phosphatidylethanolamine) to the initial formulation, to produce a freeze-dried material containing said intermediate; the antigen, containing a suitable complementary reactive moiety (e.g. thiol), can then be linked, by reacting the respective reactive moieties, to the intermediate compound already incorporated in the envelope of the reconstituted microbubbles.

In the case of the process disclosed in WO2004/069284, the construct containing the antigen can also be admixed with the components of the initial mixture, undergoing to the emulsion and lyophilisation steps. Alternatively, a micellar suspension containing the construct can be separately prepared and subsequently added to the already formed emulsion (containing the other film-forming components), preferably under heating. As above, instead of the formed construct, a functionalized intermediate can alternatively be used, which can then be reacted at any step of the process (e.g. in the emulsion phase or upon reconstitution of the lyophilized compound) with an antigen containing a complementary reactive moiety. According to an embodiment, a functionalized envelope-forming component (or envelope-forming/spacer intermediate construct) is added as a micellar suspension to the formed emulsion, under agitation. A compound comprising the antigen (containing the complementary reactive moiety) is then added to the obtained emulsion.

For example, one may add a micellar suspension of a maleimide derivative of an envelope-forming component (such as DSPE-maleimide or DSPE-PEG-maleimide) to the formed emulsion of film forming components. Then, a solution of a mercaptoacetylated antigen (e.g. protein G, 10 mg/mL in DMF), which has been incubated in deacetylation solution (50 mM sodium phosphate, 25 mM EDTA, 0.5 M hydroxylamine.HCl, pH 7.5) is added to the emulsion, under gentle agitation, before lyophilization of the emulsion. Alternatively, the emulsion containing the maleimide derivative of the envelope-forming component is lyophilized and then the unprotected antigen is subsequently added to the reconstituted suspension of gas-filled microvesicles.

According to an alternative embodiment, the antigen can be covalently bound to gas-filled microcapsules. Preferred examples of microcapsules are those having a stabilizing envelope comprising a polymer, preferably a biodegradable polymer, or a biodegradable water-insoluble lipid (such as tripalmitine) optionally in admixture with a biodegradable polymer. Examples of suitable microcapsules and of the preparation thereof are disclosed, for instance in U.S. Pat. Nos. 5,711,933 and 6,333,021, herein incorporated by reference in their entirety. Microcapsules having a proteinaceous envelope, i.e. made of natural proteins (albumin, haemoglobin) such as those described in U.S. Pat. No. 4,276,885 or EP-A-0 324 938 (here incorporated by reference), can also be employed. The antigen can be incorporated into the microcapsules envelope by covalently binding it to an envelope-forming component of the microcapsules, according to the preparation methods illustrated above, or by admixing to the components forming the microcapsules envelope an amphiphilic component, as those previously illustrated, covalently bound to said antigen.

Any biocompatible gas, gas precursor or mixture thereof may be employed to fill the above microvesicles (hereinafter also identified as "microvesicle-forming gas").

The gas may comprise, for example, air; nitrogen; oxygen; carbon dioxide; hydrogen; nitrous oxide; a noble or inert gas such as helium, argon, xenon or krypton; a low molecular weight hydrocarbon (e.g. containing up to 7 carbon atoms), for example an alkane such as methane, ethane, propane, butane, isobutane, pentane or isopentane, a cycloalkane such as cyclobutane or cyclopentane, an alkene such as propene, butene or isobutene, or an alkyne such as acetylene; an ether; a ketone; an ester; halogenated gases, preferably fluorinated gases, such as or halogenated, fluorinated or perfluorinated low molecular weight hydrocarbons (e.g. containing up to 7 carbon atoms); or a mixture of any of the foregoing. Where a halogenated hydrocarbon is used, preferably at least some, more preferably all, of the halogen atoms in said compound are fluorine atoms.

Fluorinated gases are preferred, in particular perfluorinated gases. Fluorinated gases include materials which contain at least one fluorine atom such as, for instance fluorinated hydrocarbons (organic compounds containing one or more carbon atoms and fluorine); sulfur hexafluoride; fluorinated, preferably perfluorinated, ketones such as perfluoroacetone; and fluorinated, preferably perfluorinated, ethers such as perfluorodiethyl ether. Preferred compounds are perfluorinated gases, such as $SF_6$ or perfluorocarbons (perfluorinated hydrocarbons), i.e. hydrocarbons where all the hydrogen atoms are replaced by fluorine atoms, which are known to form particularly stable microbubble suspensions, as disclosed, for instance, in EP 0554 213, which is herein incorporated by reference.

The term perfluorocarbon includes saturated, unsaturated, and cyclic perfluorocarbons. Examples of biocompatible, physiologically acceptable perfluorocarbons are: perfluoroalkanes, such as perfluoromethane, perfluoroethane, perfluoropropanes, perfluorobutanes (e.g. perfluoro-n-butane, optionally in admixture with other isomers such as perfluoro-isobutane), perfluoropentanes, perfluorohexanes or perfluoroheptanes; perfluoroalkenes, such as perfluoropropene, perfluorobutenes (e.g. perfluorobut-2ene) or perfluorobutadiene; perfluoroalkynes (e.g. perfluorobut-2-yne); and perfluorocycloalkanes (e.g. perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane). Preferred saturated perfluorocarbons include, for example, $CF_4$, $C_2F_6$, $C_3F_8$, $C_4F_8$, $C_4F_{10}$, $C_5F_{12}$ and $C_6F_{12}$.

It may also be advantageous to use a mixture of any of the above gases in any ratio. For instance, the mixture may comprise a conventional gas, such as nitrogen, air or carbon dioxide and a gas forming a stable microbubble suspension, such as sulfur hexafluoride or a perfluorocarbon as indicated above. Examples of suitable gas mixtures can be found, for instance, in WO 94/09829, which is herein incorporated by reference. The following combinations are particularly preferred: a mixture of gases (A) and (B) in which the gas (B) is a fluorinated gas, selected among those previously illustrated, including mixtures thereof, and (A) is selected from air, oxygen, nitrogen, carbon dioxide or mixtures thereof. The amount of gas (B) can represent from about 0.5% to about 95% v/v of the total mixture, preferably from about 5% to 80%.

Particularly preferred gases are $SF_6$, $C_3F_8$, $C_4F_{10}$ or mixtures thereof, optionally in admixture with air, oxygen, nitrogen, carbon dioxide or mixtures thereof.

In certain circumstances it may be desirable to include a precursor to a gaseous substance (i.e. a material that is capable of being converted to a gas in vivo). Preferably the gaseous precursor and the gas derived therefrom are physiologically acceptable. The gaseous precursor may be pH-activated, photo-activated, temperature activated, etc. For example, certain perfluorocarbons may be used as temperature activated gaseous precursors. These perfluorocarbons, such as perfluoropentane or perfluorohexane, have a liquid/gas phase transition temperature above room temperature (or the temperature at which the agents are produced and/or stored) but below body temperature; thus, they undergo a liquid/gas phase transition and are converted to a gas within the human body.

As mentioned previously, the microvesicles of the invention are particularly useful as vaccine and/or immunomodulating formulations.

The Applicant has observed in particular that the microvesicles of the invention, where the antigen is covalently bound thereto (and preferably microvesicles comprising at least 50% by weight of phospholipids in their stabilizing envelope) are particularly effective in the uptake by antigen-presenting cells, in particular dendritic cells, as compared to microvesicles where the antigen is not covalently bound thereto (e.g. encapsulated or adsorbed). As observed by the Applicant, said increased uptake results in a higher production of specific antibodies against the covalently-bound antigen, as well as an increase in antigen-specific T cell responses. Without willing to be bound to any particular theory, it may be hypothesized that, in the microvesicles of the invention, the antigen is more effectively taken up by the antigen-presenting cells.

In view of their advantageous adjuvant effect on promoting/modulating immune responses, the microvesicles of the invention can be used for effectively administering any of the previously listed (vaccine) antigens covalently bound thereto. Administration of microvesicles can be performed, for instance, by subcutaneous, intradermal, transdermal, intramuscular or intravenous injections or by mucosal routes, such as oral, sublingual, nasal, intra-bladder, vaginal or rectal delivery. Administrations, up to e.g. a total number of five, can be done at intervals comprised, for instance, between 2 weeks and 6 months. The composition is preferably administered in the form of an aqueous suspension of gas-filled microvesicles. Alternatively, the composition can be administered as a lyophilisate or as a gel solution.

An example of a protocol of injection/immunization is presented in the working examples herein.

The microvesicles of the invention can thus be used in any medical treatment comprising or inducing a modulation of the immune response in a patient in need thereof, in particular a treatment for modulating the immune response in a patient in need thereof. Typically, the treatment comprises vaccination of the patient.

For instance, the immunomodulating treatment may include treatment of infections (typically bacterial, viral, parasitic and/or fungal infections such as, for instance, malaria, meningitis, measles, AIDS, flu (influenza), cholera or listeriosis), treatment of tumors (such as, for instance, breast, prostate, lung, ovarian, bladder or esophageal cancer, sarcoma or melanoma,;) and treatments of allergies, including e.g. environmental or nutritional allergies (such as, for instance, pollen, bee venom, dust mite, latex, milk (lactose), peanuts and/or eggs (albumen) allergies.)

The following examples will help to further illustrate the invention.

Materials

The following materials and abbreviations are used in the subsequent examples:

| | |
|---|---|
| DSPC | Distearoylphosphatidylcholine (Genzyme) |
| Palmitic acid | Palmitic acid, Hexadecanoic acid (Fluka) |
| DSPE-PEG2000-mal | Distearoylphosphatidylethanolamine modified with PEG2000-maleimide (Avanti Polar lipids) |
| MPLA | Monophosphoryl Lipid A (Avanti Polar Lipid) |
| Traut reagent | 2-Iminothiolane hydrochloride (Pierce) |

-continued

| | |
|---|---|
| PEG4000 | Polyethyleneglycol 4000S from Clariant |
| Cyclooctane | Fluka |
| Ellman's reagent | 5,5'-Dithio-bis-(2-nitrobenzoic acid), (Pierce) |
| OVA | Albumin from chicken egg white grade V (Sigma) |
| Alum | Aluminum hydroxide—Al(OH)$_3$ (Sigma) |
| Cy3 | Cyanine 3 (Amersham Bioscience) |
| Trypan blue | Invitrogen |
| PBS | Phosphate buffer saline (Büchsel AG) |
| CD3 (PE*Cy7-conjugated) | B D Biosciences |
| MHC II (FITC-conjugated) | B D Biosciences |
| CD11c (APC-conjugated) | B D Biosciences |
| CD4 (PE-conjugated) | B D Biosciences |
| CD8 (Alexa647-conjugated) | B D Biosciences |
| DAPI | 4',6'-diamidino-2-phenylindole (Invitrogen) |
| CFSE | Carboxyfluorescein succinimidylester (Sigma) |
| CD4 T cell hybridoma BO97.11 | hybridoma specific for the peptide OVA$_{323-339}$; obtained from P. Marrack (Howard Hughes Medical Institute, Denver, CO) |
| DC2.4 | Dendritic cell line; obtained from K. L. Rock (University of Massachusetts Medical School, Worcester, MA) |
| DC1940 | Dendritic cell line; obtained from H. Acha-Orbea (University of Lausanne, Lausanne, Switzerland) |
| IgG (HRP conjugated) | Sigma-Aldrich |
| IgG1 (biotin conjugated) | Invitrogen |
| IgG2a (biotin conjugated) | Invitrogen |
| Extravidin-HRP | Sigma-Aldrich |
| TMB (HRP substrate) | B D Bioscience |
| DTT | Dithiotreitol (Biorad) |
| PLA2 | Phospholipase A2 Apis mellifera (Latoxan) |
| Urea | Fluka |

EXAMPLE 1

Preparation of Gas-Filled Microvesicles Comprising a Covalently-Bound Antigen (OVA)

Thiolation of OVA

OVA (6 mg-133 nmoles) was dissolved in PBE (Phosphate buffer 25 mM, 150 mM saline, 1 mM EDTA, pH 8) to obtain a solution at 20 mg/mL. A solution of Traut reagent (2 mg/mL-14.5 mM) was prepared in PBE and 92 μL of this solution (10 equ.) were added to the OVA solution. The resulting mixture was incubated at room temperature for 1 h under stirring. This solution was spun through a spin-column (Zeba spin column 2 mL, Pierce, #89890) equilibrated in PBE. The final volume of the solution was of about 390 μL.

The final OVA concentration (measured by UV at 280 nm) was about 300 nmol./mL

The thiolated OVA solution was used immediately after purification to limit possible oxidation of the thiols.

Preparation of Microvesicles with Covalently Bound OVA:

DSPE-PEG-maleimide (6.6 mg-2.24 μmoles) was dissolved in phosphate buffer 100 mM pH 6 (0.5 mL) at 45° C. with stirring (vortex) to obtain a clear solution.

60 mg of a mixture of DSPC/Palmitic acid (80/20 by moles) were dissolved in cyclooctane (4.8 mL) at 70° C. Separately, the micelle solution prepared above (0.5 mL) was added to 59.5 mL of PEG4000 10% solution. The organic phase containing the phospholipids was then added to the aqueous phase and emulsified by using a high speed homogenizer (Megatron MT3000) for 5 min (11,500 rpm), to obtain an emulsion. The emulsion was divided in 10 mL fractions in PP tubes (Falcon-15 mL).

Thiolated OVA (78 nmoles-260 μL) was added to 10 mL of the emulsion and the resulting mixture was agitated at 22° C. for 3 h. The obtained emulsion was finally diluted twice with 10% PEG4000 solution and sampled in DIN4R vials (500 μL per vial). Vials were frozen at −50° C. for 2 h (Christ Epsilon lyophilizer), then freeze-dried at −25° C. and 0.2 mBar for 12 h. The lyophilized product was then exposed to an atmosphere containing 35% of perfluoro-n-butane and 65% of air.

The product was dispersed in a volume of saline (1 mL, 150 mM NaCl) by gentle hand shaking.

EXAMPLE 2

Preparation of Gas-Filled Microvesicles Comprising a Covalently-Bound Antigen (OVA) and an Adjuvant Microbubbles were prepared according to example 1 except that 8.1 mg of MPLA (5% molar ratio) were added in the DSPC/AP mixture before dissolution in cyclooctane.

EXAMPLE 3

In-Vitro Internalization of Antigen Covalently Linked to Gas-Filled Microvesicles by Murine Dendritic Cells In order to test the ability of murine CD11c$^+$ dendritic cells (DC) to internalize an antigen covalently linked to microvesicles, spleens from Balb/c mice were collected and processed to single cell suspension prior to positive selection using anti-CD11c mAb/magnetic bead technology (Miltenyi Biotech). Enriched CD11c$^+$ cells were seeded for 2 h in poly-L-lysine-coated microtiter plates and then incubated for 3 h at 37° C. with OVA covalently linked to microvesicles or microvesicles without antigen (prepared as in Example 1), where OVA was fluorescently labeled with Cy3 dye. Microtiter plates were inverted during the incubation time with DC in order to promote cell-microvesicles contact. Indeed, gas-filled microvesicles, instead of sedimenting, move up once in solution. The cells were then collected, washed with PBS and then incubated with Trypan blue in PBS in order to quench fluorescence related to Cy3:OVA (that might be adsorbed at the cell surface of DC). With this approach, the fluorescent signal associated to the cells only reflected that of OVA endocytosed by DC. Then, cells were labeled with mAbs against CD3 (PE*Cy7-conjugated), MHC II (FITC-conjugated) and CD11c (APC-conjugated), washed and analyzed by flow cytometry. DAPI was used to exclude dead cells. Percentages of DAPI$^-$CD3$^-$CD11c$^+$ MHC II$^+$Cy3$^+$ cells were calculated and the mean fluorescence intensity (MFI) of Cy3 signal in DAPI$^-$CD3$^-$CD11c$^+$ MHC II$^+$ cells was measured using a LSR II flow cytometer (BD Biosciences).

The experiment was performed independently with cells recovered from 3 mice (table 1) and the results obtained showed that under these conditions 31.2±9.4% of cells, analyzed as mentioned above, are Cy3$^+$ in presence of Cy3:OVA covalently linked to microvesicles, whereas only 1.0±0.7% of cells were Cy3$^+$ using control plain microvesicles. Internalization of Cy3:OVA covalently linked to microvesicles was also apparent when Cy3 signal MFI was analyzed. Indeed, when DC were incubated with Cy3:OVA covalently linked to microvesicles, the MFI of Cy3 signal (879.7±95.1) was significantly higher than that observed with control microvesicles (92.3±7.5).

TABLE 1

| | % Cy3+ cells | | MFI Cy3 signal | |
|---|---|---|---|---|
| | Control microvesicles | Cy3:OVA-microvesicles | Control microvesicles | Cy3:OVA-microvesicles |
| Mouse 1 | 0.8 | 28.3 | 100 | 915 |
| Mouse 2 | 0.4 | 23.5 | 92 | 772 |
| Mouse 3 | 1.7 | 41.7 | 85 | 952 |
| Mean ± SD | 1.0 ± 0.7 | 31.2 ± 9.4 | 92.3 ± 7.5 | 879.7 ± 95.1 |

TABLE 2

| | EC50 (µM) | | | |
|---|---|---|---|---|
| | Free OVA | OVA-cov. microvesicles | OVA-latex beads | OVA ads.-microvesicles |
| Experiment 1 | 13.15 | $3.09 \cdot 10^{-3}$ | $1.71 \cdot 10^{-2}$ | $5.33 \cdot 10^{-2}$ |
| Experiment 2 | 15.00 | $3.51 \cdot 10^{-3}$ | $2.10 \cdot 10^{-2}$ | $2.14 \cdot 10^{-2}$ |
| Experiment 3 | 2.36 | $7.90 \cdot 10^{-3}$ | $5.52 \cdot 10^{-3}$ | $2.29 \cdot 10^{-2}$ |
| Experiment 4 | 3.99 | $8.44 \cdot 10^{-3}$ | $5.87 \cdot 10^{-3}$ | $1.95 \cdot 10^{-2}$ |
| Mean | 8.63 | $5.74 \cdot 10^{-3}$ | $1.24 \cdot 10^{-2}$ | $2.93 \cdot 10^{-2}$ |

EXAMPLE 4

In-Vitro Antigen Presentation to Murine CD4 T Cells: Comparison Between Antigen Covalently Linked to Microvesicles and Antigen not Covalently Bound to Microvesicles Adherent murine DC1940 cell line (25,000 cells/well) were seeded for 2 h in microtiter plates and then incubated for 4 h at 37° C. with titrated concentrations of OVA in different formulations diluted in PBS: (a) $OVA_{323-339}$ peptide (control peptide: fragment of OVA binding directly to MHC class II molecules expressed on the membrane of dendritic cells; peptide:MHC class II complexes are presented to CD4 T cells, without need for internalization and processing), (b) OVA, (c) OVA covalently linked to microbubbles prepared according to example 1, (d) OVA linked to latex beads or (e) OVA adsorbed on cationic microvesicles (20% DSTAP) by mixing both components for 10 minutes. When microvesicles were used, microtiter plates were inverted during the period of incubation with DC1940 cells in order to promote cell-microvesicles contact. After the coincubation period, the cells were collected, washed with PBS, counted using a Neubauer chamber under a microscope and mixed (25,000 cells/well) with CD4 T cell hybridoma BO97.11 (20,000 cells/well) for 24 h. Supernatant was harvested by pipetting and IL-2 production, indicative of T cell activation, was quantified by Enzyme-Linked ImmunoSorbent Assay (ELISA).

Based on the titration curves obtained—OVA concentrations (agonist) vs. OD 450 nm (response), a sigmoid fitting curve was generated using GraphPad Prism 5.03 software. The OVA concentration giving half maximal OD 450 nm for each curve was then calculated (EC50), that enables a comparison of each experimental condition tested. The results of table 2 show that OVA covalently linked to microbubbles was much more efficiently presented to CD4 T cells than any other OVA formulation tested. In particular, it can be observed that the EC50 obtained with microvesicles containing the covalently bound antigen is more than 4000 times lower (p=0.0159) than that of free OVA, 10 times lower (p=0.0357) than that of OVA conjugated to latex beads and more than 10 times lower (p=0.0357) than that of OVA adsorbed on cationic microvesicles. In other words, this means that less OVA is needed to achieve half of the maximal CD4 T cell activation with OVA covalently linked to microvesicles as compared to the other formulations tested. Accordingly, OVA covalently linked to microvesicles induces an activation of CD4 T cells already at OVA concentrations of about $1 \cdot 10^{-3}$ µM. On the contrary, concentrations of $1 \cdot 10^{-2}$ µM or above are necessary to activate CD4 T cells when OVA is conjugated to latex beads or adsorbed on cationic microvesicles. Up to 1 µM of free antigen induces negligible activation of Tcells.

EXAMPLE 5

Comparison of T cell Responses Generated In Vivo Upon Administration of Antigen Covalently Linked to Microvesicles, Antigen Alone and Antigen+Alum Adjuvant The ability and efficiency of antigen-containing microvesicles of the invention to generate an in vivo T cell immune response was evaluated by injecting the microvesicles subcutaneously to Balb/c mice. The results were compared with the injection of similar amounts of the antigen molecule alone and combined with Alum.

OVA covalently linked to microvesicles prepared according to example 1 was injected 3 times at 2-week intervals into mice that were sacrificed 14 days after the last injection and spleen was collected from each mouse and processed to obtain single cell suspensions. OVA-specific CD4 and CD8 T cell responses were evaluated by the carboxyfluorescein succinimidyl ester (CFSE)-based proliferation assay, as follows: splenocytes were labeled with CFSE in PBS-0.1% BSA at 37° C. and then washed with PBS-5% fetal calf serum. Splenocytes were then seeded into round-bottom 96-well plates at $5 \cdot 10^6$ cells/well and incubated with either medium alone, OVA (100 µg/mL) or concanavalin A (1.5 µg/mL) as positive control. After 2 days, 2.5 U/mL IL-2 were added to each well and 2 days later, cells were collected and washed with PBS. Cells were then labeled with mAbs against mouse CD3 (PE*Cy7-conjugated), CD4 (PE-conjugated) and CD8 (Alexa647-conjugated), washed, and DAPI was finally added shortly prior to analysis by flow cytometry. As the CFSE dye is diluted when cells are dividing, we recorded the percentage of $CFSE^{low}$ $CD3^+$ $CD4^+$ $DAPI^-$ or $CFSE^{low}$ $CD3^+CD8^+DAPI^-$ cells as cells having responded to the stimuli added. Results are expressed as stimulation index (SI), which are calculated as the frequency of cells responding to OVA divided by the frequency of cells responding to medium alone.

Experimental settings were similar to those described in Example 3.

As presented in table 3, SI measured after 3 injections of OVA covalently linked to microvesicles induced both CD4 and CD8 T cell responses superior to those induced by injection of free OVA. This is represented by significantly higher SI of CD4 and CD8 T cells responding to OVA in mice that have received OVA covalently linked to microvesicles (11.08 and 7.98, respectively) as compared to SI obtained for the same populations in mice injected with free OVA (2.82 and 2.07, respectively; p=0.0022 for CD4 T cells and p=0.0022 for CD8 T cells). In addition, OVA-specific CD4 T cell responses were similar when mice received OVA covalently linked to microvesicles (11.08) or OVA admixed with Alum (10.30; p=0.9360). The calculated SI after a 4-days stimulation in vitro reflect the frequencies arising in vivo. Therefore the data presented above demonstrate a superior ability of OVA covalently linked to MB to induce in vivo OVA-specific CD4 and CD8 T cell responses over free OVA. It also shows that the reagents presented by the Applicant are as potent as the adjuvant Alum at inducing CD4 T cell responses.

TABLE 3

| CD4 T cells | | | CD8 T cells | | |
|---|---|---|---|---|---|
| OVA-microvesicles | OVA alone | OVA/Alum | OVA-microvesicles | OVA alone | OVA/Alum |
| 11.08 | 2.82 | 10.30 | 7.98 | 2.07 | 14.35 |

EXAMPLE 6

Comparative In Vivo Antibody Response Upon Administration of Antigen Covalently Linked to Gas-Filled Microvesicles, Antigen Alone and Antigen+Alum Adjuvant The ability and efficiency of antigen-containing microvesicles of the invention to generate an in vivo antibody immune response was evaluated by injecting the microvesicles subcutaneously to Balb/c mice. The results were compared with the injection of similar amounts of the antigen alone and with the injection of the antigen mixed with Alum adjuvant.

OVA covalently linked to microvesicles prepared according to example 1 was injected at 2 weeks intervals into mice, and sera were collected after the $2^{nd}$ and after the $3^{rd}$ injection, to evaluate the presence of OVA-specific antibodies. The presence and titers of OVA-specific antibodies (total IgG in table 2) were determined by ELISA according to the following protocol. Briefly, Maxisorb plates (Nunc) were coated with 10 μg/mL OVA, blocked with PBS-0.05% Tween 20-1% BSA and washed before addition of titrated doses of sera. Following overnight incubation at 4° C., plates were washed and the presence of OVA-specific IgG was assessed by incubation with HRP-coupled anti-IgG antibody. Following washing, HRP substrate was added and the reaction was stopped after a few minutes with 1M $H_2SO_4$ and OD 450 nm was measured. Based on the titration curves obtained (sera dilutions (agonist) vs. OD 450 nm (response)), a sigmoid fitting curve was generated using GraphPad Prism 5.03 software and the three parameters log (agonist) vs. response function. The serum dilution (titer) giving half maximal OD 450 nm for each curve was then calculated (EC50), that enables a comparison of each condition tested.

The results obtained with the administration of OVA-containing microvesicles were compared with the results obtained in similar in vivo tests by administering either OVA alone or OVA mixed with Alum adjuvant (a standard adjuvant used since more than 7 decades in human vaccines).

To this extent 100 μL of OVA-containing preparations, corresponding to 8 μg of antigen, was injected three times at two-week intervals, subcutaneously at the base of the tail of mice (six per experimental group). Mice from the OVA group were injected with OVA diluted in PBS. Mice from the OVA microvesicle group were injected with the preparation reconstituted in 1 mL of PBS with gentle hand mixing. Prior to injections, hand mixing was repeated. Mice from the OVA/Alum group were injected with a solution of OVA and Alum diluted in PBS and mixed on a rotating wheel for 30 minutes. Prior to injection, the preparation was washed with PBS. The final amount of Alum administered to each mouse was 1 mg.

As shown in table 4, the IgG EC50 titers (mean) measured after the injection of OVA covalently linked to microvesicles (after either two or three injections) was significantly higher (p=0.0247 and p=0.0260, respectively; Mann-Whitney test) with respect to the one observed for OVA alone. Furthermore, the IgG titers obtained with OVA-microvesicles compared with those obtained using OVA admixed with the Alum adjuvant (p=0.3939 after two injections and p=0.9372 after three injections; Mann-Whitney test).

These results mean that to get a similar amount of Ab detected by ELISA, less diluted sera from mice immunized with free OVA are required, as compared to those from mice immunized with OVA covalently linked to MB or OVA adsorbed on the Alum adjuvant. Therefore, more Ab are produced in vivo in response to OVA covalently linked to MB, over free OVA, giving an advantage to the reagents proposed by the Applicant.

TABLE 4

| | OVA-microves. | OVA alone | OVA/Alum |
|---|---|---|---|
| IgG titer after 2 injections | 7252 | 2507 | 3406 |
| IgG titer after 3 injections | 13720 | 3969 | 14029 |

EXAMPLE 7

Comparative In Vivo Antibody Response Upon Administration of Antigen Covalently Linked to Gas-Filled Microvesicles Containing or Not the Immunomodulator MPLA The addition of an adjuvant to the antigen-containing microvesicles of the invention was evaluated by injecting the microvesicles containing MPLA subcutaneously to Balb/c mice. The results were compared with the injection of similar amounts of antigen-containing microvesicles without MPLA.

OVA covalently linked to microvesicles and containing MPLA prepared according to example 2 was injected at 2 weeks intervals into mice, and sera were collected after the $2^{nd}$ and after the $3^{rd}$ injection, to evaluate the presence of OVA-specific antibodies. The presence and titers of OVA-specific antibodies (total IgG in table 5) were determined by ELISA, as described in example 6.

The presence and titers of OVA-specific IgG1 and IgG2a antibodies (table 6) were determined by ELISA according to the following protocol. Briefly, Maxisorb plates (Nunc) were coated with 10 μg/mL OVA, blocked with PBS-0.05% Tween 20-1% BSA and washed before addition of titrated doses of sera. Following overnight incubation at 4° C., plates were washed and the presence of OVA-specific IgG1 and IgG2a was assessed by incubation with biotinylated anti-IgG1 or anti-IgG2a antibodies. Plates were then washed and further incubated with extravidin-HRP. Following washing, HRP substrate was added and the reaction was stopped after a few minutes with 1M H2SO4 and OD 450 nm was measured. Based on the titration curves obtained (sera dilutions (agonist) vs. OD 450 nm (response)), a sigmoid fitting curve was generated using GraphPad Prism 5.03 software and the three parameters log(agonist) vs. response function. The serum dilution (titer) giving half maximal OD 450 nm for each curve was then calculated (EC50), that enables a comparison of each condition tested. The ratio between OVA-specific IgG1 and IgG2a antibody titers was calculated for each mice using EC50 values obtained for each IgG subtype and then the mean was calculated for each experimental group.

The results obtained with the administration of OVA-microvesicles containing MPLA were compared with the results obtained in similar in vivo tests by administering antigen-containing microvesicles without MPLA.

100 μL of OVA-containing preparations, corresponding to 8 μg of antigen, was injected three times at two-week intervals, subcutaneously at the base of the tail of mice (six per experimental group).

As shown in table 5, the IgG EC50 titers (mean) measured after the injection of MPLA-OVA-microvesicles (after either two or three injections) was significantly higher (p=0.0043 and p=0.0087, respectively; Mann-Whitney test) with respect to the one observed for OVA-microvesicles. Noteworthy, The antibody titer after two injections with the MPLA-OVA formulation is higher that the titer obtained after three injections with OVA-microvesicles.

TABLE 5

|  | MPLA-OVA-microves. | OVA-microves |
|---|---|---|
| IgG titer after 2 injections | 59692 | 18437 |
| IgG titer after 3 injections | 76023 | 33229 |

Table 6 shows that the ratio between IgG1 and IgG2a titers was significantly lower after injection of MPLA-OVA-microvesicles compared to OVA-microvesicles (p=0.0152; Mann-Whitney test).

TABLE 6

|  | MPLA-OVA-microves. | OVA-microves |
|---|---|---|
| IgG1 titer after 3 injections | 112154 | 55839 |
| IgG2a titer after 3 injections | 50940 | 9408 |
| IgG1/IgG2a ratio | 2.29 | 6.71 |

These results demonstrate that, although more antibodies are produced in vivo in response to OVA covalently linked to microvesicles as compared to OVA alone (shown in example 6), the formulation containing MPLA yielded even higher antibody titers.

Additionally, the type of immune response was different for OVA-microvesicles containing or not MPLA: in presence of MPLA, IgG1/IgG2a ratio was lower, suggesting a shift toward a Th1-type immune response.

EXAMPLE 8

T Cell and Antibody Responses Generated In Vivo After Administration of Antigen Covalently Linked to Microvesicles in the C57BL/6 Mouse Strain.

The ability of antigen-containing microvesicles of the invention to generate an in vivo T cell and Ab immune response was further evaluated by injecting the microvesicles subcutaneously to C57BL/6 mice. The results were compared with the injection of similar amounts of the microvesicle formulation in Balb/c mice.

Microvesicles with covalently-bound OVA prepared according to example 1 were injected 3 times at 2-week intervals into mice that were sacrificed 14 days after the last injection. Blood and spleen were collected from each mouse and analyzed for the presence of OVA-specific Ab and T cell responses according to the protocol described in Examples 5 and 6.

SI measured after 3 injections of microvesicles induced both CD4 and CD8 T cell responses similar to those induced by injection of the same formulation in Balb/c mice (table 7). In both strains, the administration of microvesicles with covalently-bound antigen yielded significantly higher SI than those obtained with injection of control microvesicles without antigen (p=0.0087 for Balb/c mice and p=0.0286 for C57BL/6 mice for CD4 T cell responses, and p=0.0050 for Balb/c mice and p=0.0286 for C57BL/6 mice for CD8 T cells, respectively).

TABLE 7

|  | C57BL/6 | | Balb/c | |
|---|---|---|---|---|
|  | Control microvesicles | OVA microvesicles | Control microvesicles | OVA microvesicles |
| CD4 T cells | 3.01 | 8.83 | 2.23 | 9.00 |
| CD8 T cells | 1.43 | 7.08 | 0.73 | 10.55 |

Similar results were obtained when quantifying total OVA-specific IgG in serum. Injection of OVA covalently linked to microvesicles induced significantly higher levels of Ab in both mice strains as compared to control injection performed with plain microvesicles (p=0.0050 for Balb/c mice and p=0.0286 for C57BL/6 mice). Equivalent IgG titers were also observed between both strains. Additionally, analysis of OVA-specific IgG1 and IgG2a Ab demonstrated similar titers of both isotypes in immunized Balb/c and C57BL/6 (table 8).

TABLE 8

|  | C57BL/6 | | Balb/c | |
|---|---|---|---|---|
|  | Control microvesicles | OVA microvesicles | Control microvesicles | OVA microvesicles |
| IgG | 102 | 17762 | 103 | 13720 |
| IgG1 | 102 | 34468 | 101 | 48316 |
| IgG2a | 102 | 5226 | 102 | 3632 |

These results show that the microvesicles of the invention, when injected 3 times subcutaneously at 2-week intervals significantly induce Ag-specific Ab and T cell responses, independently of the mouse strain studied.

EXAMPLE 9

Preparation of Gas-Filled Microvesicles Comprising a Covalently-Bound Antigen

A) Denaturation of PLA2 Antigen

PLA2 (1 mg-54.05 nmoles) was dissolved in a denaturant solution of Urea (540.54 g/L-9 M in PBE) to obtain a solution at 4 mg/mL. A solution of DTT (8 mg/mL-51.86 mM) was prepared in Urea 9 M and 104 μL (100 equ.) of this solution were added to the PLA2 urea solution. The resulting mixture was left overnight (16 hours) at room temperature. This solution was spun through a spin-column (Zeba spin column 2 mL, Pierce, #89890) equilibrated in PBE. The final volume of the solution was of about 350 μL.

The denatured PLA2 solution was used immediately after purification.

B) Preparation of Microvesicles with Covalently Bound PLA2:

PLA2-containing microvesicles were prepared according to the methodology illustrated in example 1.

Thus 10 mL of the emulsion prepared according to example 1 (containing DSPC/Palmitic acid and DSPE-PEG-maleimide) were admixed with 10 or 20 nmoles (154 μL or 308 μL) of denatured PLA2.

After dilution and lyophilization, the product was dispersed in a volume of saline (1 mL, 150 mM NaCl) by gentle hand shaking, for subsequent use

EXAMPLE 10

T Cell and Antibody Responses Generated In Vivo After Administration of PLA2 Antigen Covalently Linked to Microvesicles The ability of antigen-containing microvesicles of the invention to generate an in vivo T cell and Ab immune response was evaluated by subcutaneously injecting the microvesicles prepared according to example 9 to Balb/c mice.

Microvesicles prepared according to example 9 were injected at 2-week intervals into mice, and sera and spleens were collected after the $3^{rd}$ injection to evaluate the presence of OVA-specific antibodies and T cells. The protocol was the same as the one described in Examples 5 and 6, except that OVA was replaced by PLA2.

The results obtained with the administration of covalently-bound PLA2 antigen microvesicles were compared with the results obtained with administration of control microvesicles that did not contain the antigen.

As shown in table 9, the SI measured after the three injections of PLA2 covalently linked to microvesicles were significantly higher than those obtained in mice that had received control microvesicles. This was true for both CD4 and CD8 T cell responses (p=0.0238 and p=0.0275, respectively). Similarly, total PLA2-specific IgG titers were also measured at a level significantly superior to the one obtained by administration of microvesicles lacking the antigen (p=0.0238).

TABLE 9

|  | Control microvesicles | PLA2-microvesicles |
|---|---|---|
| SI CD4 T cells | 2.13 | 13.22 |
| SI CD8 T cells | 1.00 | 24.27 |
| IgG titers | 101 | 2146 |

These results show that the microvesicles of the invention serve as an Ag carrier to induce potent T cell and Ab immune responses independently of the nature of the antigen that is covalently linked to them.

EXAMPLE 11

Immunization with Antigen-Carrying Microvesicles Reduces Bacterial Load in Mice deliberately Infected with a Pathogenic Bacterium The ability of immune responses induced by administration of antigen-containing microvesicles of the invention to reduce the bacterial load after infection with OVA-expressing Listeria monocytogenes was evaluated in C57BL/6 mice.

Microvesicles prepared according to example 1 or control microvesicles were injected subcutaneously 3 times at 2-week intervals into C57BL/6 mice. Two weeks after the last administration, 50,000 OVA-expressing Listeria monocytogenes were injected intravenously to infect both immunized and control mice. Mice were sacrificed four days after bacterial infection and spleens were collected to assess bacterial load. To do so, spleens were lysed in PBS containing 0.1% Nonidet P40 and meshed through a 40 μm cell strainer to obtain homogenized spleen suspensions. Serial 1:10 dilutions of the latter were applied on brain-heart-infusion/agarose bacteria culture plates containing streptomycin and incubated for 36 h at 37° C. Colony forming units were counted on plates and bacterial load per spleen was calculated.

Results in table 10 demonstrate that immunization of mice with OVA antigen-containing microvesicles of the invention generate a specific immune response efficient enough to reduce by a remarkable 120-fold factor the bacterial load found in the spleen of these mice as compared to mice administered with control microvesicles (p=0.0152), indicating that partial protection takes place in this highly sensitive model.

TABLE 10

|  | Control microvesicles | OVA-microvesicles |
|---|---|---|
| Bacterial load (CFU/spleen) | $4.22 \cdot 10^7$ | $8.01 \cdot 10^5$ |

The invention claimed is:

1. An immunomodulating treatment method comprising administering to a patient in need thereof a pharmaceutical formulation comprising gas-filled microvesicles with a stabilizing envelope, said microvesicles comprising an antigen covalently bound to a component of said envelope,
   wherein the method is performed with no ultrasound irradiation.

2. The method according to claim 1 wherein said treatment comprises vaccination.

3. The method according to claim 2 wherein said antigen is a vaccine antigen.

4. The method according to claim 1 wherein said treatment comprises a tolerance-inducing treatment.

5. The method according to claim 1 wherein said treatment comprises an immunostimulating treatment.

6. The method according to claim 1 wherein said component is a phospholipid.

7. The method according to claim 6 wherein said phospholipid is a pegylated phospholipid.

8. The method according to claim 1 wherein said antigen is present in a molar amount of from 0.1% to 20% in said envelope.

9. The method according to claim 1 wherein the gas contained in the microvesicles comprises a fluorinated gas.

10. The method according to claim 9 wherein said gas is in admixture with air or nitrogen.

11. The method according to claim 1 wherein said stabilizing envelope comprises at least 50% by weight of a phospholipid.

12. The method according to claim 1 wherein said envelope further comprises an immunomodulating adjuvant.

13. The method according to claim 12 wherein said adjuvant represents from 0.1% to about 50% by mole of the envelope.

14. The method according to claim 1 wherein said antigen is selected from the group consisting of an allergenic antigen, a viral antigen, a bacterial antigen, a fungal antigen, a toxin-derived antigen, a parasitic antigen, a self antigen, a tumor antigen and a mixture thereof.

15. The method according to claim 1 wherein the pharmaceutical formulation comprises an aqueous suspension comprising said gas-filled microvesicles.

16. The method according to claim 15 wherein said aqueous suspension comprising said gas-filled microvesicles is prepared by reconstituting a precursor of said suspension in the form of a dry powdered material with a physiologically acceptable aqueous carrier.

17. A method of vaccinating comprising
administering to a patient in need thereof a suspension of gas-filled microvesicles, with a stabilizing envelope, said microvesicles comprising an antigen covalently bound to a component of said envelope,
wherein the method is performed with no ultrasound irradiation.

18. The method according to claim 17 wherein said microvesicles provide an effective uptake by antigen-presenting cells.

19. A method for increasing the uptake of an antigen by a respective antigen-presenting cell, which comprises contacting said antigen with said cell wherein said antigen is covalently bound to a gas-filled microvesicle,
wherein the method is performed with no ultrasound irradiation.

20. A method according to claim 19, wherein said antigen-presenting cell is a dendritic cell.

* * * * *